US010300257B2

(12) United States Patent
Wu et al.

(10) Patent No.: US 10,300,257 B2
(45) Date of Patent: May 28, 2019

(54) FEATURES TO ENHANCE GRIP OF BALLOON WITHIN AIRWAY

(71) Applicant: Acclarent, Inc., Irvine, CA (US)

(72) Inventors: Show-Mean Wu, Fremont, CA (US); Tapan Mistry, Fremont, CA (US); Dexter D. Hernando, Union City, CA (US); Siddhi K. Desai, San Jose, CA (US); Robert J. Tannhauser, Bridgewater, NJ (US); Shrirang V. Ranade, Foster City, CA (US); Ketan P. Muni, Irvine, CA (US); Martin J. Madden, New Hope, PA (US); Andrew Chen, Fremont, CA (US)

(73) Assignee: Acclarent, Inc., Irvine, CA (US)

( * ) Notice: Subject to any disclaimer, the term of this patent is extended or adjusted under 35 U.S.C. 154(b) by 291 days.

(21) Appl. No.: 15/083,482

(22) Filed: Mar. 29, 2016

(65) Prior Publication Data
US 2016/0279398 A1 Sep. 29, 2016

Related U.S. Application Data

(62) Division of application No. 13/796,073, filed on Mar. 12, 2013, now abandoned.

(51) Int. Cl.
*A61M 29/02* (2006.01)
*A61M 25/10* (2013.01)
*A61B 17/3207* (2006.01)

(52) U.S. Cl.
CPC ..... *A61M 29/02* (2013.01); *A61B 17/320725* (2013.01); *A61M 25/104* (2013.01);
(Continued)

(58) Field of Classification Search
CPC ........ A61B 17/320725; A61M 25/104; A61M 29/02
See application file for complete search history.

(56) References Cited

U.S. PATENT DOCUMENTS

| 5,423,745 A | 6/1995 | Todd et al. |
| 6,033,380 A * | 3/2000 | Butaric ............ A61M 25/1002 604/103.07 |

(Continued)

FOREIGN PATENT DOCUMENTS

| WO | WO 00/57815 | 10/2000 |
| WO | WO 2010/001405 | 1/2010 |

OTHER PUBLICATIONS

International Search Report and Written Opinion dated Sep. 2, 2014 re Application No. PCT/US2014/018046.

*Primary Examiner* — Tuan V Nguyen
(74) *Attorney, Agent, or Firm* — Frost Brown Todd LLC

(57) ABSTRACT

A dilation assembly includes a shaft and a dilator coupled with the distal end of the shaft. The dilator includes a proximal end, a distal end, and a center portion positioned between the proximal end and the distal end. The center portion dilates from a first configuration to a second configuration. The center portion has a larger diameter than the proximal end and the distal end when the center portion is in the second configuration. At least one gripping feature is positioned on at least a portion of the exterior surface of the center portion. The gripping feature provides friction between the center portion and a bodily lumen when the center portion is in the second configuration.

20 Claims, 16 Drawing Sheets

(52) U.S. Cl.
CPC .............. *A61M 2025/109* (2013.01); *A61M 2025/1072* (2013.01); *A61M 2025/1075* (2013.01); *A61M 2025/1086* (2013.01); *A61M 2025/1088* (2013.01); *A61M 2210/1025* (2013.01)

(56) References Cited

U.S. PATENT DOCUMENTS

| | | |
|---|---|---|
| 6,306,144 B1 | 10/2001 | Sydnet et al. |
| 6,478,807 B1 | 11/2002 | Foreman et al. |
| 6,506,202 B1 | 1/2003 | Dutta et al. |
| 6,635,078 B1 | 10/2003 | Zhong et al. |
| 6,736,841 B2 | 5/2004 | Musbach et al. |
| 7,947,758 B2 | 5/2011 | Khatri |
| 8,016,849 B2 | 9/2011 | Wenchell |
| 8,262,687 B2 | 9/2012 | Igaki |
| 2004/0126526 A1* | 7/2004 | Parsonage ............ A61M 25/104 428/36.91 |
| 2005/0149082 A1* | 7/2005 | Yee ................. A61B 17/32072 606/159 |
| 2008/0110961 A1 | 5/2008 | Voegele et al. |
| 2009/0318863 A1* | 12/2009 | Chen ..................... A61M 25/10 604/103.01 |
| 2010/0168511 A1 | 7/2010 | Muni et al. |
| 2011/0004057 A1 | 1/2011 | Goldfarb et al. |
| 2013/0116798 A1 | 5/2013 | Farrar et al. |
| 2013/0197619 A1 | 8/2013 | Ishii |
| 2014/0277071 A1 | 9/2014 | Wu et al. |

\* cited by examiner

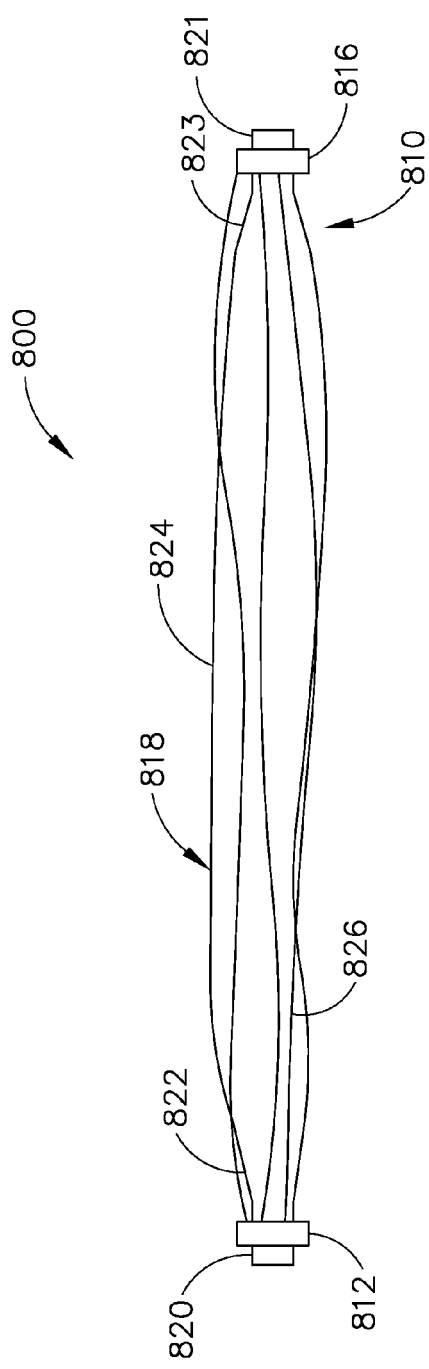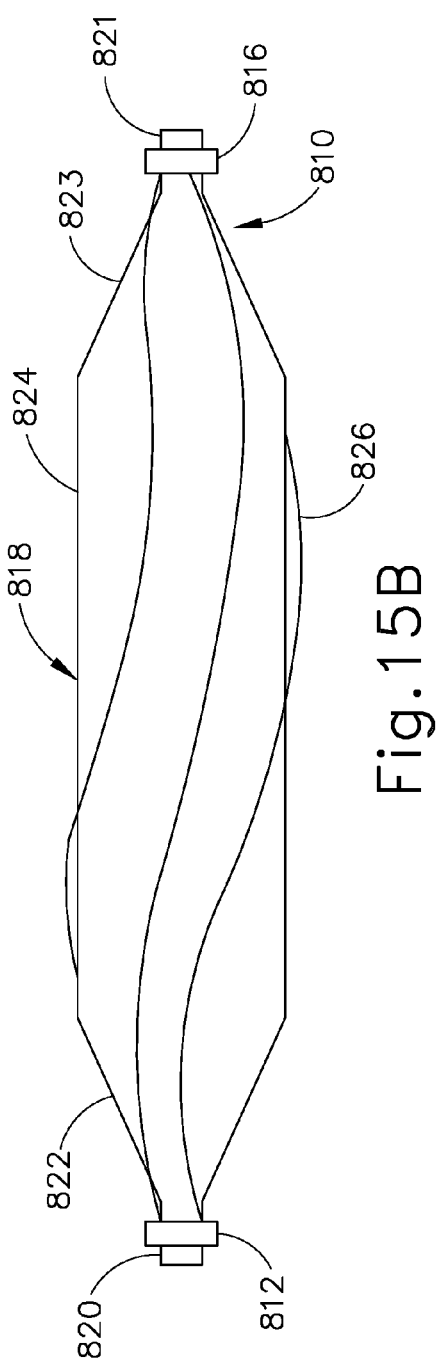
Fig.15A
Fig.15B

FEATURES TO ENHANCE GRIP OF BALLOON WITHIN AIRWAY

This application is a division of U.S. patent application Ser. No. 13/796,073, entitled "Features to Enhance Grip of Balloon Within Airway," filed on Mar. 12, 2013, published as U.S. Publication No. 2014/0277071 on Sep. 18, 2014, now abandoned.

BACKGROUND

In some instances, it may be desirable to dilate an anatomical passageway in a patient. This may include dilation of ostia of paranasal sinuses, dilation of a patient's airway (e.g., to treat a stenosis within the larynx), dilation of the nasal cavity, dilation of the Eustachian tube, dilation of other passageways within the ear, nose, or throat, dilation of blood vessels, dilation of the urethra, etc. One method of dilating anatomical passageways includes using a guide wire and catheter to position an inflatable balloon within the anatomical passageway, then inflating the balloon with a fluid (e.g., saline) to dilate the anatomical passageway.

Airway stenosis (or "airway narrowing") is a medical condition that occurs when some portion of a patient's airway becomes narrowed or constricted, thus making breathing difficult. A stenosis may occur in any part of the airway including the larynx, trachea, bronchi, or a combination of any of the above mentioned regions. Both adults and children may develop a stenosis. In some instances, a stenosis is caused by intubation, which is when a tube is placed in the airway for ventilation/breathing assistance in a patent who cannot breathe. Intubation for prolonged periods of time may traumatize the airway, causing scar tissue formation that forms the stenosis.

Therapies for treating an airway stenosis range from endoscopic treatments, such as dilation and laser resection, to open procedures, such as laryngotracheal reconstruction. In one technique, a series of rigid dilators of increasing diameter are pushed down the airway, gradually expanding the constriction but also applying shear forces to the airway. Balloon catheters may also be used to perform dilation of an airway or other anatomical passageway. For instance, the expandable balloon may be positioned within a stenosis in an airway (e.g., larynx, trachea, bronchi, etc.) and then be inflated, to thereby dilate the airway and increase airflow. The dilated airway may then allow for improved breathing. Once the balloon is deflated or subjected to negative pressure, however, the balloon may tend to lose its shape and become flat, folded, or otherwise non-cylindraceous. An example of a system that may be used to perform dilation procedures is described in U.S. Pub. No. 2010/0168511, entitled "System and Method for Dilating an Airway Stenosis," published Jul. 1, 2010, issued as U.S. Pat. No. 9,913,964 on Mar. 13, 2018, the disclosure of which is incorporated by reference herein.

While several airway dilation systems have been made and used, it is believed that no one prior to the inventor(s) has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 15A depicts a side view of another exemplary balloon having gripping features for use in the system of FIG. 1 in a collapsed configuration;

FIG. 15B depicts a side view of the balloon of FIG. 15A in an expanded configuration;

Figure 1:
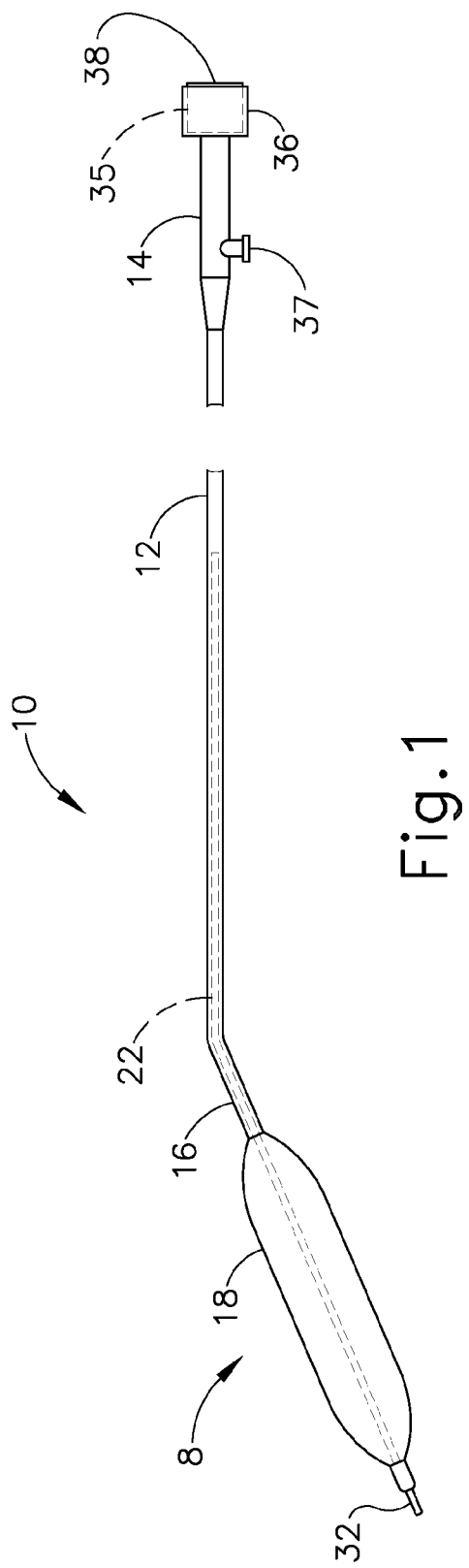
FIG. 1 depicts a side view of an exemplary system for dilating a stenosis in the airway, including a balloon catheter and a stylet.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Balloon Dilation Catheter System

FIG. 1 shows an exemplary dilation catheter system (8), which may be used to dilate a stenosis in an airway; or to dilate some other anatomical passageway (e.g., within the ear, nose, throat, cardiovascular system, etc.). At least part of system (8) may be constructed and operable in accordance with at least some of the teachings of U.S. Pub. No. 2010/0168511, issued as U.S. Pat. No. 9,913,964 on Mar. 13, 2018, the disclosure of which is incorporated by reference herein. It should be understood that dilation catheter system (8) may be used to dilate either a naturally occurring passageway in a patient or a surgically created passageway in a patient.

Dilation catheter system (8) of this example comprises a balloon catheter (10) and a stylet (22). Balloon catheter (10) comprises a shaft (12) positioned between a hub (14) and a balloon (18). Balloon (18) is coupled to a distal end of shaft (12) and is configured to receive fluid through balloon catheter (10). Stylet (22) is slidably positioned through balloon catheter (10). In some versions, at least a portion of stylet (22) has a greater stiffness than at least a portion of balloon catheter (10), such that when stylet (22) is bent and inserted within balloon catheter (10), balloon catheter (10) at least partially conforms to the shape of stylet (22). In a dilation procedure, stylet (22) is used to advance balloon catheter (10) within an airway or targeted anatomical passageway (e.g., at a stenosis site). Balloon (18) may then be actuated to an expanded state to open or dilate the targeted anatomical passageway. Balloon (18) may then be actuated back to a collapsed state such that balloon (18) is deflated. This process may be repeated to dilate several anatomical passageways.

A. Exemplary Balloon Catheter

As shown in FIG. 1, balloon catheter (10) comprises a catheter shaft (12). An inflatable balloon (18) is attached to a distal end of shaft (12) via adhesive or other attachment means. A hub (14) is coupled to a proximal end of shaft (12) and comprises a stylet port (38) and an inflation port (37). Stylet (22) is inserted within stylet port (38) and generally resides within an inner lumen of shaft (12). Fluid (e.g., saline, etc.) is introduced through inflation port (37) through shaft (12) to inflate balloon (18).

Balloon catheter (10) may have any number of suitable sizes, shapes and configurations. For example, balloon (18) may have different lengths and diameters in different embodiments, to accommodate different patient anatomies. The overall catheter (10) length and diameter may also vary. For example, the overall length of balloon catheter (10) (i.e., from the proximal end of hub (14) to the distal end of catheter shaft (12)) is about 35-70 cm, such as less than or equal to about 50 cm, or about 45 cm.+−0.5 cm. Catheter (10) may be handled and manipulated with one hand. The working length of balloon (18) in FIG. 1 is about 40 mm+/−0.2 mm. By "working length" it is meant the length between the two tapered portions of balloon (18). In some versions, the working length of balloon (18) may range from between about 10 mm and about 60 mm such as about 16-45 mm. The outer diameter of the fully inflated working length of balloon (18) may also vary. In the present example, balloon (18) has an inflated diameter of about 14.1 mm+/−0.5 mm. In some versions, balloon (18) diameter may range from about 3 mm to about 24 mm, such as about 5-15 mm. A combination of balloon diameters and lengths may be provided, such that a physician may choose an appropriate size for an adult or pediatric patient. In one example, the following balloon diameters and lengths may be provided: 5 mm by 24 mm; 7 mm by 24 mm; 10 mm by 40 mm; and 14 mm by 40 mm. Of course, any of a number of other combinations of sizes of balloons (58) may be provided.

Any suitable material may be used to form balloon (18). Balloon (18) may be compliant, semi-compliant or non-compliant. Balloon (18) may be made of nylon, some other polymer, such as PTFE, and/or any other suitable material(s). In some versions, balloon (18) is formed of an elastic/extensible material that is resiliently biased to assume a shrunken, non-inflated configuration, such that the material forming balloon (18) is under increased tension when balloon (18) is in a non-deflated state. In some other versions, balloon (18) is formed of a material that is flexible yet substantially inelastic/non-extensible, such that the material forming balloon does not provide a significant resilient bias. In other words, balloon (18) does not stretch in response to increased fluid pressure inside balloon (18), even though the effective outer diameter of balloon (18) increases in response to increased fluid pressure. Such inelastic versions of balloon (18) may nevertheless be filled with fluid, with the fluid pressure being increased to provide an outwardly directed force via balloon (18), and this process may be referred to as "inflating." When the pressure of fluid inside balloon (18) is reduced, this process may be referred to as "deflating," even if the material forming balloon (18) does not elastically shrink, since balloon (18) may nevertheless flexibly collapse in response to reduced fluid pressure. Thus, it should be understood that the use of terms like "inflate," "inflated," "deflate," and "deflated" does not necessarily mean that the material forming balloon (18) undergoes any elastic stretching or shrinking as the fluid pressure within balloon (18) changes.

In some versions, balloon (18) may include an outer slip-resistant surface, which may be formed by a textured surface or a coating. Such a surface may help prevent slipping of balloon (18) out of an airway structure during inflation and/or may facilitate re-wrapping balloon (18) by hand after deflation if balloon (18) is to be used for a second or subsequent dilation procedure. Examples of such balloons are discussed in more detail below.

Catheter shaft (12) may also be formed of any suitable material. It may be desirable to form shaft (12) from material(s) selected so that shaft (12) is unlikely to kink when bent, such as when bent by stylet (22) and/or a user. One such material, for example, is Pebax, although other polymers may be used. Shaft (12) may also have any suitable color and may include one or more shaft markings. The shaft color and markings may be built into shaft (12) by using a colored material or may be added by applying paint or another colorant. In some versions, shaft (12) may have a dark color, such as black or dark blue, and one or more light colored markings may be applied over the dark shaft (12). In some versions, the markings (not shown) may include direct visualization markings (viewed directly with the naked eye or an endoscope) and/or radiographic markings (viewed with a radiographic device such as intraoperative fluoroscopy). Any suitable combination, size and color of markings may be used. One example of shaft color and shaft markings, which could be used or modified for a balloon catheter, is the Relieva Solo Pro™ Sinus Balloon Catheter, manufactured by Acclarent, Inc. of Menlo Park, Calif.

B. Exemplary Stylet

Figure 2:
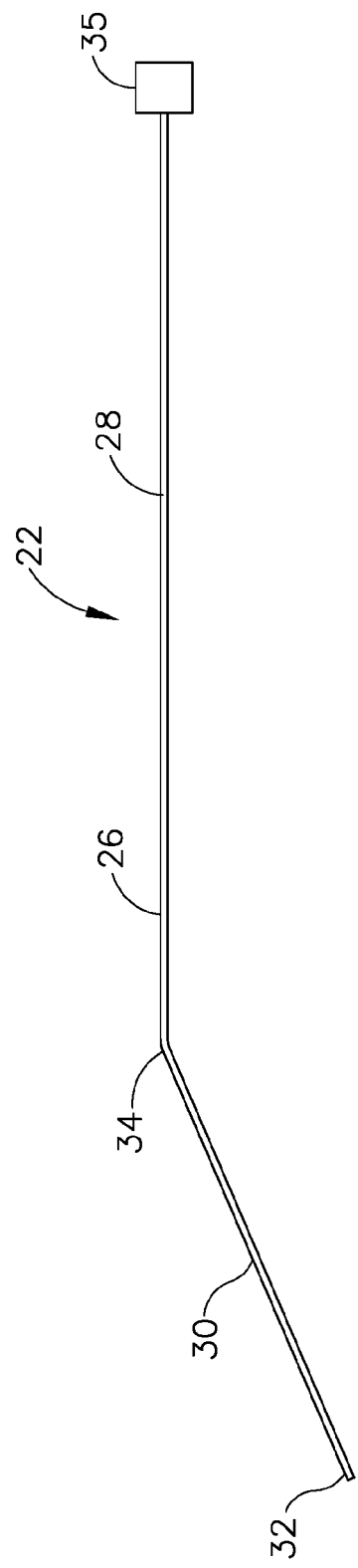
FIG. 2 depicts a side view of the stylet of FIG. 1.

FIG. 2 shows stylet (22) in greater detail. Stylet (22) comprises a core member (26) with a proximal section (28) and a distal section (30). A coil (32) is disposed around at least part of distal section (30) of core member (26). A luer lock member (35) is coupled with a proximal end of core member (26) for coupling with a hub on balloon catheter (10). In some versions, stylet (22) does not include a coil (32). Core member (26) and/or coil (32) may be formed of nitinol, stainless steel, or other biocompatible materials. Distal portion (30) of stylet (22) includes a bend or curve (34) that is stiff enough to bend balloon catheter (10) during the placement of balloon catheter (10) within the airway of the patient. In some versions, stylet (22) may be provided in a generally straight configuration. Stylet (22) may be preformed to have a bend (34), or stylet (22) may be malleable, such that a user may bend stylet (22) and stylet (22) maintains the user-created bend. This malleability allows a user to adjust a bend angle according to the airway anatomy of a particular patient. Proximal section (28) of stylet (22) may be generally stiff, a distal section (30) may be generally malleable, and an extreme distal portion may be atraumatic and very flexible or even floppy. This variation in flexibility along the length of stylet (22) may be achieved by using different materials, such as stainless steel and nitinol. Alternatively, one material, such as stainless steel, may be used and the diameter of stylet (22) may be altered to achieve the variation in flexibility along the length of stylet (22).

Stylet (22) has an overall length approximately as long or slightly longer than balloon catheter (10). In some versions, stylet (22) includes an atraumatic, flexible distal tip portion that extends distally out of balloon catheter (10) when stylet (22) is fully disposed within catheter (10). This tip portion may be, for example, between about 0.25 cm to about 8 cm (e.g., about 1-5 cm) in length; and may facilitate the ability of a user to advance system (8) through a patient's airway atraumatically. The overall length of stylet (22) may vary from about 30 cm to about 80 cm, such as from about 45 cm to about 60 cm. Of the overall length, a flexible distal portion of stylet (22) may be from about 5-20 cm, such as from about 10-15 cm. Bend (34) may have any suitable angle, such as from greater than 0 degrees to about 20 degrees. The diameter of stylet (22) may be less than about 1.3 mm, such as 0.9 mm or less. The diameter may decrease distally to about 0.13 mm+/−0.013 mm. Of course, the foregoing dimensions are mere examples. Any other suitable dimensions may be used.

Stylet (22) may be attached to balloon catheter (10), or stylet (22) may be removably connected to balloon catheter (10). Stylet (22) comprises a luer lock member (35) with threads on proximal section (28) that screw into opposing threads disposed on a luer (36) of balloon catheter (10). In some versions, balloon catheter (10) may include a locking mechanism (not shown) to lock stylet (22) in position within catheter (10). The locking mechanism can be any mechanical device, including a lever, a ball and pin, a luer, etc. All or part of distal section (30) of stylet (22) may extend out of the distal end of catheter (10). Stylet (22) may be locked to balloon catheter (10) at different positions or lengths so the distal end of stylet (22) extends out of or is positioned within balloon catheter (10) at different lengths. The length, diameter(s) and stiffness characteristics of stylet (22) may be varied in different embodiments to confer different performance characteristics to the overall system (8).

Use of stylet (22) to insert balloon catheter (10) helps to guide the distal end of balloon catheter (10) through the airway of the patient and to the stenotic region. Stylet (22) provides increased steerability during advancement of balloon catheter (10). Torquability of balloon catheter (10) is also increased when using stylet (22). In some versions, luer lock member (35) of stylet (22) and luer (36) of balloon catheter (10) mate together, so that stylet (22) and balloon catheter (10) may be rotated together and thus steered into a constricted portion of an airway.

In some versions, stylet (22) may have a light emitting portion, such as a light emitting distal end or tip. For example, stylet (22) may include one or more light fibers to transmit light from a light source attached to the proximal end of stylet (22) to its distal end. Light from a light emitting stylet (22) may be used to help a user visualize a patient's airway from the inside using a scope and/or in some cases from the outside via transillumination through the patient's skin. A light emitting guidewire device that may be used or modified to achieve such an illuminating stylet (22) is the Relieva Luma™ Sinus Illumination Guidewire/System, manufactured by Acclarent, Inc. of Menlo Park, Calif. Such an illuminating stylet (22) may have any of the features described above with the additional feature of light emitting capability.

C. Exemplary Method of Use of the System

Figure 3A:
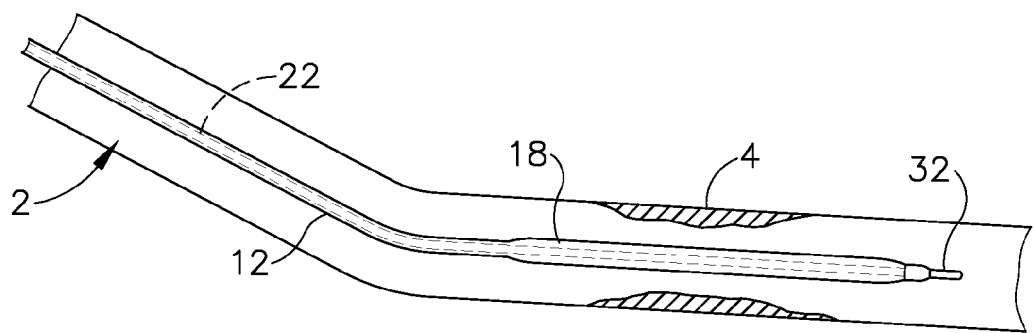
FIG. 3A depicts a cross sectional view of the system of FIG. 1 being introduced into an airway, with the balloon positioned at a stenosis in a collapsed state.
Figure 3B:
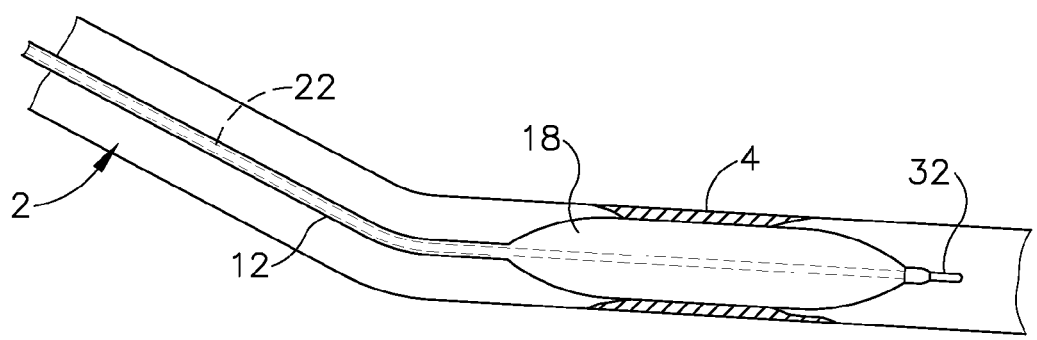
FIG. 3B depicts a cross sectional view of the system of FIG. 3A, with the balloon inflated to a dilated state.

FIGS. 3A and 3B show a method for dilating an stenotic region (4) in an airway (2), such as in a case of subglottic stenosis. Dilation system (8) is introduced through the mouth and into the airway of the patient. Optionally, a bronchoscope (not shown) or other scope device may be used to visualize the positioning of dilation system (8). Dilation system (8) may be bent either by the user or by the manufacturer of system (8). For example, stylet (22) may be bent and then inserted into balloon catheter (10), while in other cases stylet (22) and balloon catheter (10) may be bent together, with stylet (22) already residing in catheter (10). The support of stylet (22) and the bend in the overall system (8) may help a physician navigate system (8) through the patient's airway to position balloon (18) within at least a portion of stenotic region (4). As shown in FIG. 3A, inflatable balloon (18) of the catheter (10) is in an unexpanded configuration during advancement and placement of balloon catheter (10). As shown in FIG. 3B, once balloon (18) is positioned within stenotic region (4) of the airway (2), inflatable balloon (18) is inflated to dilate stenotic region (4). Balloon (18) is then deflated to enable removal from airway (2). By way of example only, balloon (18) may be deflated by actively drawing the fluid from balloon (18); by venting the fluid in balloon (18), allowing the inward pressure imposed by airway (2) to drive fluid from balloon (18); or in any other suitable fashion as will be apparent to those of ordinary skill in the art in view of the teachings herein.

In some versions, stylet (22) remains in balloon catheter (10) during inflation of balloon (18). Maintaining stylet (22) in catheter (10) during inflation may give catheter (10) added column strength and help maintain the position of balloon (18) within stenotic region (4), thus avoiding slipping. In some versions, stylet (22) is removed from balloon catheter (10) before inflating. Stylet (22) may be removed from balloon catheter (10) after balloon catheter (10) is properly positioned within airway (2) of the patient, or stylet (22) can be removed after stenosis (4) has been dilated but before removing balloon catheter (10) from the patient.

Inflatable balloon (18) may be inflated more than once to dilate stenotic region (4) of airway (2). The physician inflates inflatable balloon (18) to a desired pressure during each dilation of stenosis (4). Proper dilation of stenotic region (4) can be confirmed by visualizing the region with the bronchoscope/endoscope.

II. Exemplary Balloon Gripping Features

The airway of each patient has a unique anatomical make-up and is coated with mucus or other bodily fluids. This may cause balloon (18) to slip a small amount during inflation, which may result in balloon (18) sliding longitudinally out of position from within stenotic region (4). Similar conditions may occur in other anatomical passageways in a patient where balloon (18) might be used (e.g., Eustachian tube, within an ostia of a patient's sinus, other passageways within the ear, nose, or throat, etc.). Accordingly, it may be desirable to provide gripping features on balloon (18) to decrease or prevent balloon (18) from slipping within the airway during inflation. The gripping features may be provided on a surface of balloon (18) or gripping elements may be added to balloon (18). Several examples of balloon gripping features are described in greater detail below, while other examples will be apparent to those of ordinary skill in the art in view of the teachings herein.

A. Exemplary Balloon Surface Gripping Features

Balloon gripping features may be incorporated into the surface of balloon (18) to increase friction between balloon (18) and a patient's airway and decrease or prevent balloon (18) from slipping within the airway. The examples below provide several versions of surface gripping features that may be readily incorporated into balloon (18).

Figure 4:
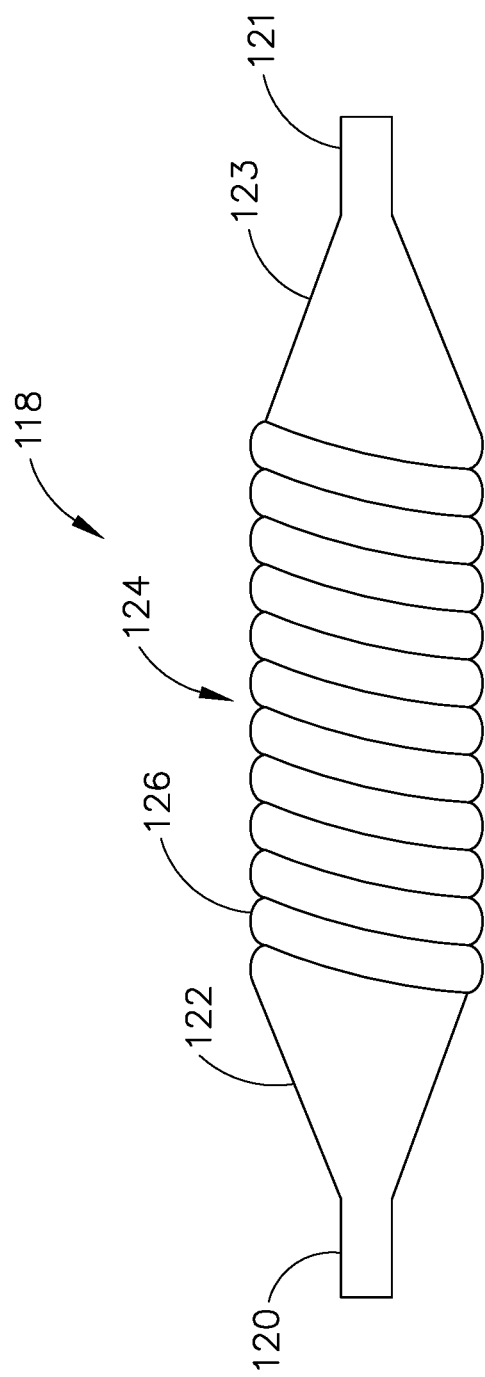
FIG. 4 depicts a side view of an exemplary balloon having gripping features for use in the system of FIG. 1.

FIG. 4 shows an exemplary balloon (118) with a corrugated surface (126). Balloon (118) comprises a proximal end (120), a working length (124), and a distal end (121). Proximal end (120) and distal end (121) are sized to attach with shaft (12) of catheter (10). Working length (124) is positioned between proximal end (120) and distal end (121). Working length (124) has a larger diameter than proximal end (120) and distal end (121) when balloon (118) is dilated and is configured to be positioned within an airway to treat a stenosis (4). A tapered portion (122) couples proximal end (120) and working length (124). A tapered portion (123) couples working length (124) and distal end (121).

Working length (124) comprises a corrugated surface (126). Corrugated surface (126) is configured with a plurality of annular ridges positioned along working length (124). Corrugated surface (126) provides hills and valleys on working length (124) to increase the friction between balloon (118) and an airway. Corrugated surface (126) may cover the entire surface of balloon (118) or may cover a portion of balloon (118). For instance, corrugated surface (126) may cover 50% of the surface of balloon (118). Corrugated surface (126) may be created by wrapping balloon (118) with a stiffer plastic or metal string to create the ridges when balloon (118) is inflated. Corrugated surface (126) may also be formed by knurling or chemically via etching. Other suitable ways in which corrugated surface (126) may be provided will be apparent to one with ordinary skill in the art in view of the teachings herein. Corrugated surface (126) may also reinforce balloon (118) against internal pressure and decrease the compliance of balloon (118). Balloon (118) may be made from nylon, polyethylene terephthalate, or any thermoplastic with similar properties. In the present example, the wall thickness of balloon (118) is about 0.001" to about 0.005". Of course, any other suitable thickness may be used.

Figure 5:
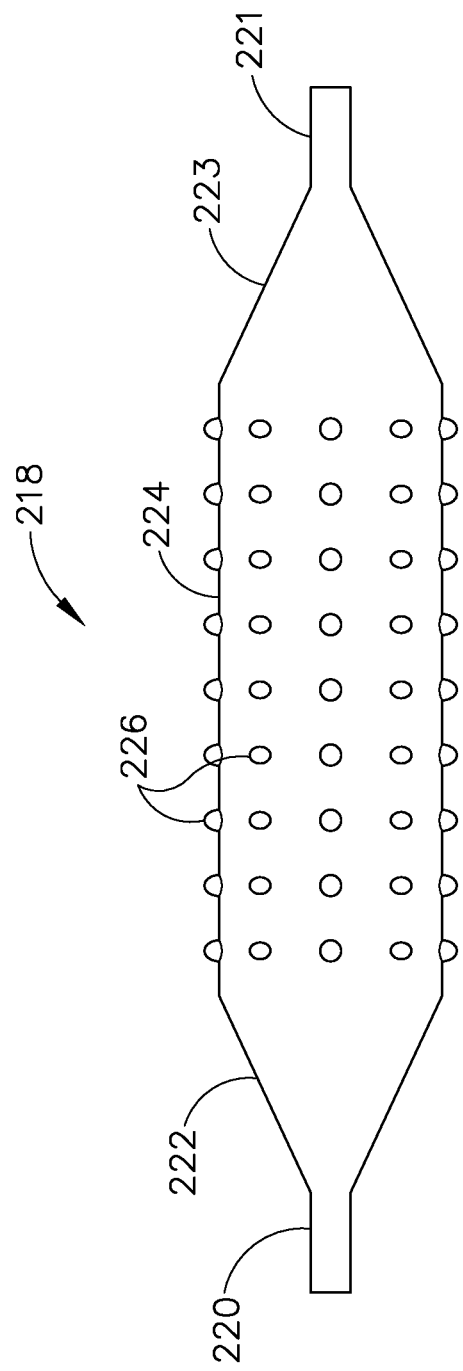
FIG. 5 depicts a side view of another exemplary balloon having gripping features for use in the system of FIG. 1.

FIG. 5 shows another exemplary balloon (218) with a knobby surface. Balloon (218) is similar to balloon (118), except that working length (224) of balloon (218) comprises a plurality of knobs (226). Knobs (226) extend outwardly from working length (224) to increase the friction between balloon (218) and an airway. Knobs (226) may cover the entire surface of balloon (218) or may cover a portion of balloon (218). For instance, knobs (226) may cover 50% of the surface of balloon (218). In the present example, knobs (226) are configured in rows positioned transversely across balloon (218). However, knobs (226) may have any configuration or pattern on balloon (218). Knobs (226) may be molded on balloon (218) such that knobs (226) expand as balloon (218) expands. Knobs (226) may also be micro-protrusions applied or mounted on the surface of balloon (218). Such micro-protrusions may be made by imprinting silicon and Ni molds. The micro-protrusions would thus maintain their shape as balloon (218) expands. Knobs (226) may also be a frictional skin formed similar to the material of a conventional Nitrile glove and may be mounted on balloon (218) in longitudinal and radial patterns. In some versions, knobs (226) are oriented obliquely and/or are in the form of barbs to further resist longitudinal movement of balloon (118) within the airway. For instance, some knobs (226) may be oriented obliquely distally to resist distal movement of balloon (118) in the airway; while other knobs (226) may be oriented obliquely proximally to resist proximal movement of balloon (118) in the airway. Other suitable knob (226) configurations will be apparent to one with ordinary skill in the art in view of the teachings herein.

Figure 6:
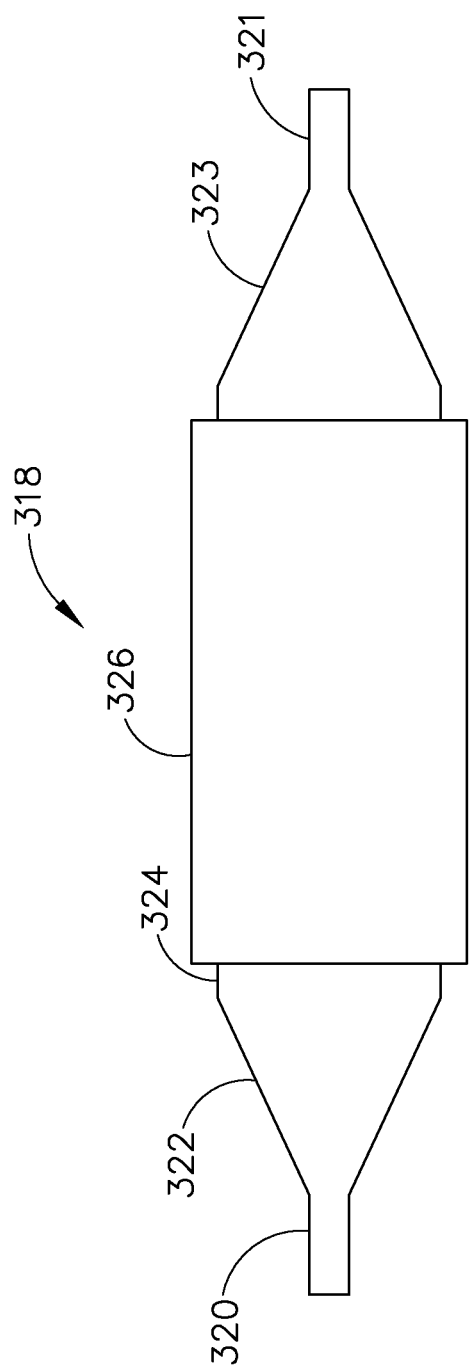
FIG. 6 depicts a side view of another exemplary balloon having gripping features for use in the system of FIG. 1.

FIG. 6 shows another exemplary balloon (318) with a coating (326). Balloon (318) is similar to balloon (118), except that working length (324) of balloon (318) comprises a coating (326). Coating (326) is a non-slip or textured coating applied to working length (324) of balloon (318) to increase the friction between balloon (318) and an airway.

Coating (326) may cover the entire surface of balloon (318) or may cover a portion of balloon (318). For instance, coating (326) may cover 50% of the surface of balloon (318). Coating (326) may comprise a thermoplastic elastomer, such as polyurethane, neoprene, or any other material having a low durometer rating and a rubber-like consistency. Coating (326) may also comprise a moisture activated, degradable tissue adhesive. Various suitable materials will be apparent to one with ordinary skill in the art in view of the teachings herein. In the present example, coating (326) has a thickness of about 0.0003" to about 0.005". Of course, any other suitable dimensions may be used. Balloon (318) may be dipped in coating (326) or coating (326) may be sprayed onto balloon (318). Other suitable ways in which coating (326) may be provided will be apparent to one with ordinary skill in the art in view of the teachings herein. Coating (326) may also reinforce balloon (318) to increase the burst strength of balloon (318) and decrease the risk of balloon (318) being inadvertently punctured.

Figure 7:
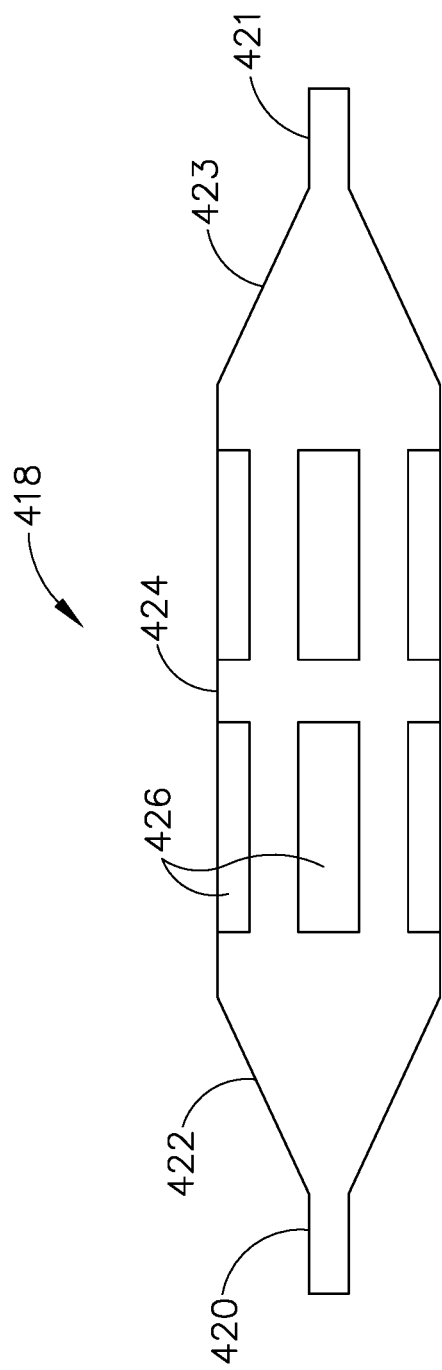
FIG. 7 depicts a side view of another exemplary balloon having gripping features for use in the system of FIG. 1.

FIG. 7 shows another exemplary balloon (418) with a non-slip material (426). Balloon (418) is similar to balloon (118), except that working length (424) of balloon (418) comprises a non-slip material (426). Material (426) is a non-slip or textured material applied to working length (424) of balloon (418) to increase the friction between balloon (418) and an airway. Material (426) may cover the entire surface of balloon (418) or may cover a portion of balloon (418). In the present example, material (426) is applied to balloon (418) in a plurality of longitudinal strips extending across the surface of balloon (418). Although strips of material (426) are used in the present example, any suitable shape of material (426) may be used (e.g., ring, circle, square, rectangle, triangle, etc.). Similarly, although material (426) is aligned in rows in FIG. 7, material (426) may also be aligned in any other suitable configuration that will be apparent to one with ordinary skill in the art in view of the teachings herein. In some versions, material (426) is a different material than balloon (418). In some other versions, material (426) has the same material composition as the material forming balloon (418), but has a different texture and/or other different properties. Material (426) may have a higher coefficient of friction than balloon (418). For instance, material (426) may be a rubber-like material (e.g., polyurethane, neoprene, etc.) or a fabric. Material (426) may be adhered to balloon (418) or applied as a coating to balloon (418). Material (426) also forms an uneven surface along balloon (418) to further increase friction. Various other suitable ways in which material (426) may be provided will be apparent to one with ordinary skill in the art in view of the teachings herein.

Figure 8:
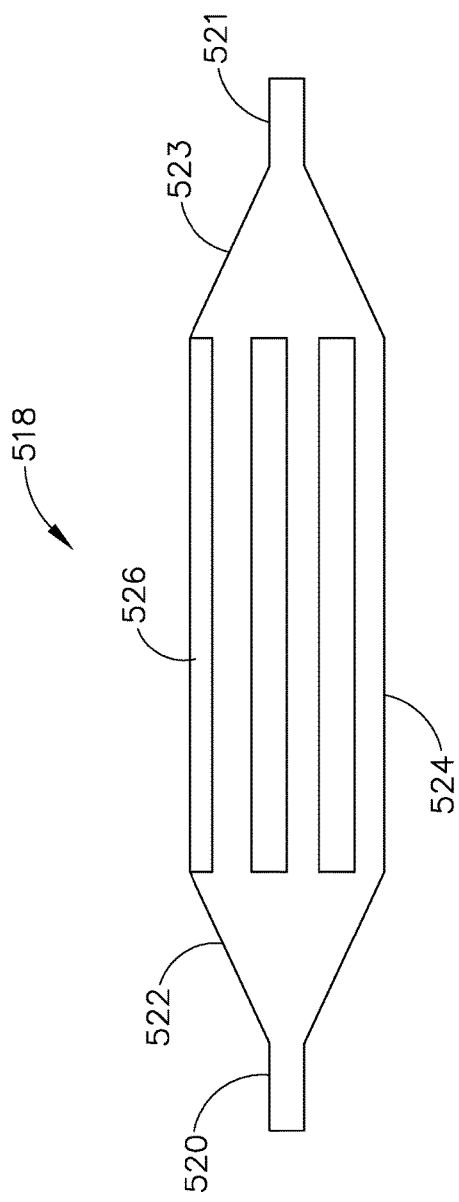
FIG. 8 depicts a side view of another exemplary balloon having gripping features for use in the system of FIG. 1.
Figure 9:
FIG. 9 depicts an end view of the balloon of FIG. 8 in a deflated configuration.

FIG. 8 shows another exemplary balloon (518) with gripping features (526). Balloon (518) is similar to balloon (118), except that gripping features (526) of are aligned in alternating longitudinal rows along working length (524) of balloon (518). Gripping features (526) may be formed from any of the gripping feature materials described above. When balloon (518) is deflated, balloon (518) is wrapped to form folds as shown in FIG. 9. Due to the alternating longitudinal rows of gripping features (526), gripping features (526) are folded underneath the exposed working length (524) surface of balloon (518) when balloon (518) is in the wrapped configuration. Gripping features (526) may be resiliently biased inwardly when balloon (518) is deflated. When balloon (518) is inflated, gripping features (526) may pivot outwardly to bear into the tissue defining the airway. Gripping features (526) may also expose a material similar to material (426) when gripping features (526) pivot outwardly. Balloon (518) is positioned within an airway in the wrapped configuration. This allows the smooth, lubricated surface of working length (524) to be exposed during positioning of balloon (518) to facilitate delivery of balloon (518) to the targeted site. Once balloon (518) is positioned, balloon (518) is inflated. When balloon (518) is inflated, as shown in FIG. 8, gripping features (526) are exposed to increase friction between balloon (518) and the airway to decrease or prevent slipping of balloon (518) within the airway. Similar to balloon (118), balloon (518) comprises a proximal end (520), a distal end (521), and tapered portions (522, 523).

B. Exemplary Balloon Gripping Elements

Gripping features may also be provided by applying gripping elements to a balloon (18) as a separate external component. The examples below provide several versions external gripping features that may be readily coupled to balloon (18).

1. Exemplary Non-Slip Elements

Figure 10:
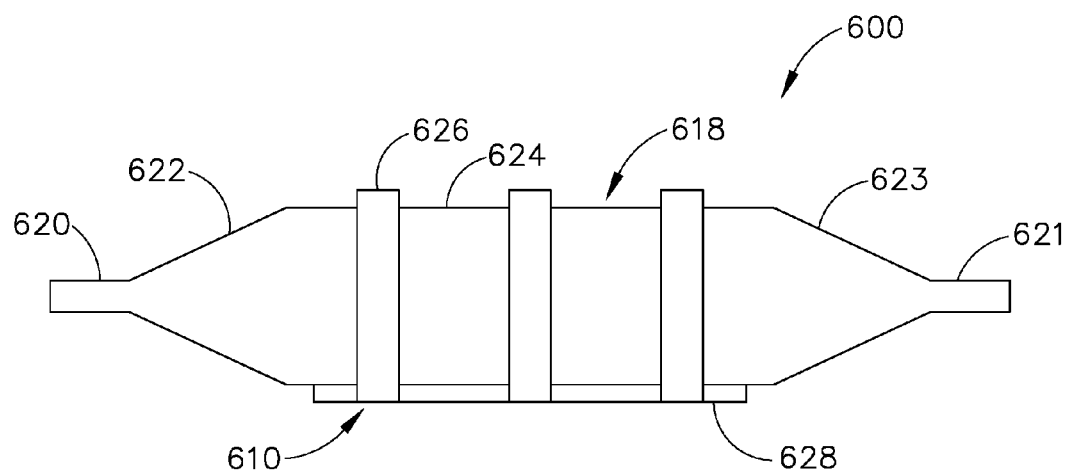
FIG. 10 depicts a side view of another exemplary balloon having gripping features for use in the system of FIG. 1.
Figure 11:
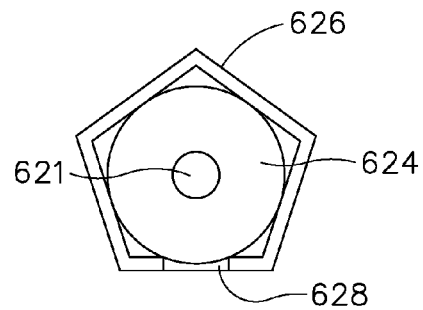
FIG. 11 depicts an end view of the balloon of FIG. 10.

FIGS. 10-13 show an exemplary gripping assembly (600). Gripping assembly (600) comprises a balloon (618), a plurality of non-slip elements (626), and a base (628). Balloon (618) is similar to balloon (18). Non-slip elements (626) are positioned around working length (624) of balloon (618). As shown in FIG. 10, non-slip elements (626) are positioned along a portion of the length of balloon (618). Although three elements (626) are shown, any number of elements may be used. For instance, one element (626) may extend continuously across balloon (618) and have a length of 30 mm; or two elements (626) may be used where each element (626) has a length of 15 mm. Elements (626) have a wall thickness of about 0.008" to about 0.0025" and are sized to correspond to the diameter of balloon (618) when balloon (618) is inflated, as shown in FIG. 11. Of course, any other suitable dimensions may be used.

Figure 12:
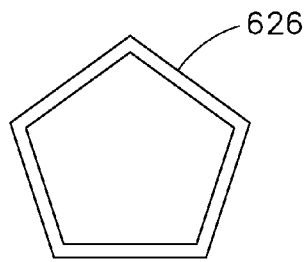
FIG. 12 depicts a front view of a gripping element of the balloon of FIG. 10.

Elements (626) may be flexible such that elements (626) expand and deflate with balloon (618). As shown in FIG. 12, element (626) is shaped as a pentagon. The corners of element (626) help to increase friction and grip an airway. Other suitable shapes (e.g., circle, triangle, square, rectangle, etc.) may be used and will be apparent to one with ordinary skill in the art in view of the teachings herein. Elements (626) may be made from stainless steel, nitinol, etc., such that elements (626) are configured to withstand bending and twisting as balloon (618) is inflated and/or deflated. Elements (626) may be at least partially encompassed by balloon (618) (e.g., covered by folds created by the outer surface of balloon (618), etc.) when balloon (618) is in a deflated state to prevent inadvertent snagging on tissue while balloon (618) is positioned within an airway. Alternatively, a sheath may be provided to cover elements (626) and balloon (618) when balloon (618) is in the deflated state while balloon (618) is positioned within the airway. The sheath could then be retracted prior to inflation of balloon (618). Other suitable ways in which elements (626) may be covered during transit within an airway will be apparent to one with ordinary skill in the art in view of the teachings herein.

Figure 13:
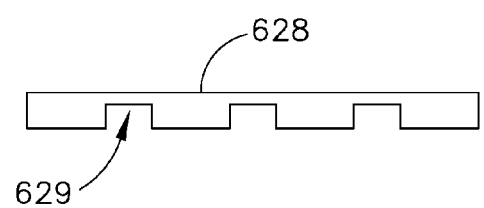
FIG. 13 depicts a side view of a base of the balloon of FIG. 10.

Elements (626) are coupled with base (628). As shown in FIG. 13, base (628) comprises a plurality of recesses (629) on a bottom surface to correspond to elements (626). As shown in FIGS. 10 and 11, base (628) is coupled to a surface of balloon (618). Elements (626) are positioned within recesses (629) and coupled to base (628) such that elements (626) wrap around balloon (618) and base (628). Base (628) thus longitudinally fixes elements (626) relative to balloon (618). Base (628) may be molded from a plastic material.

Elements (626) may be adhered to base (628), or elements (626) may be snap fitted into recesses (629). In some versions, elements (626) are adhered directly to balloon (618) such that a base (628) is not used.

2. Exemplary Net

Figure 14:
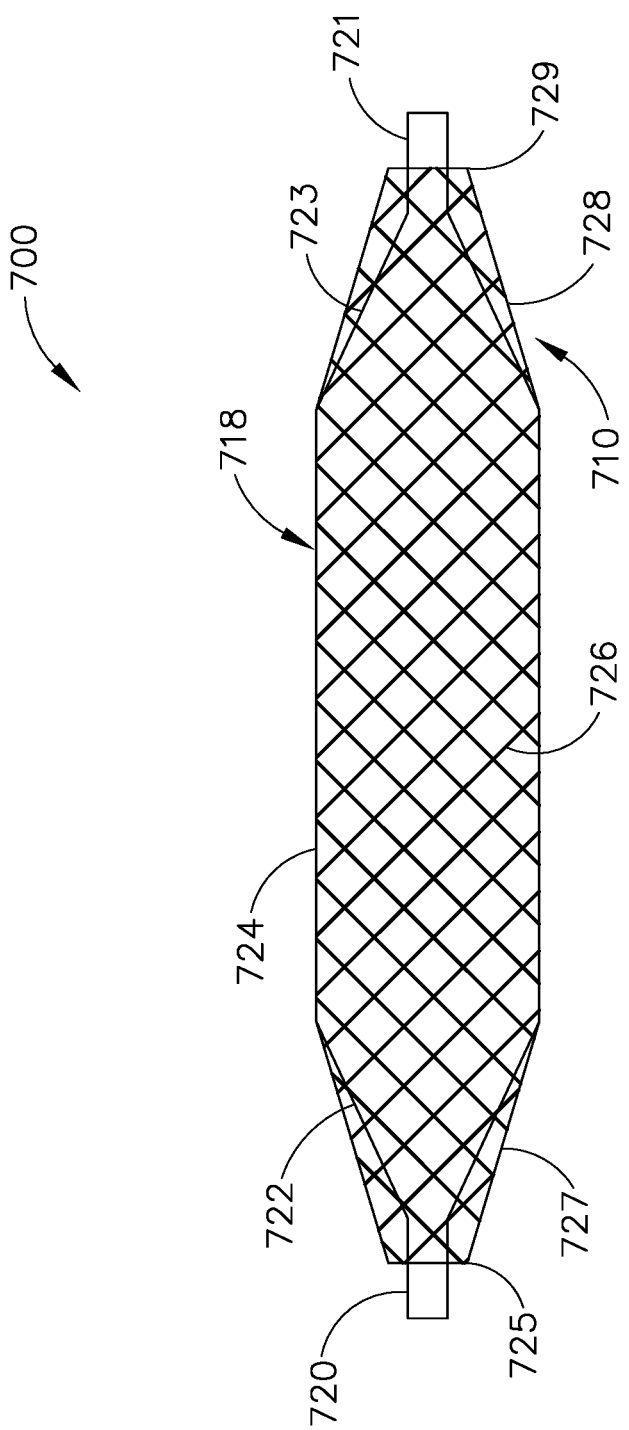
FIG. 14 depicts a side view of another exemplary balloon having gripping features for use in the system of FIG. 1.

FIG. 14 shows another exemplary gripping assembly (700). Gripping assembly (700) comprises a balloon (718) and a net (710) positioned around balloon (718). Balloon (718) is similar to balloon (18). Net (710) comprises a proximal end (725) and a distal end (729). Proximal end (725) is attached to proximal end (720) of balloon (718) and is sized to correspond to the diameter of proximal end (720). Distal end (729) is attached to distal end (723) of balloon (718) and is sized to correspond to the diameter of distal end (723). Net (710) comprises a center portion (726) positioned between proximal end (725) and distal end (729). Center portion (726) extends along the length of working length (724) of balloon (718) and is sized to correspond to the diameter of working length (724) when balloon (718) is inflated. A tapered portion (727) couples proximal end (725) of net (710) with center portion (726). Tapered portion (728) couples distal end (729) of net (710) with center portion (726). Net (710) may cover the entire surface of balloon (718) or may cover a portion of balloon (718). For instance, net (710) may cover 50% of the surface of balloon (718). Net (710) is flexible and is configured to expand and deflate with balloon (718). Net (710) may be resilient, such that net (710) returns to its original shape when balloon (718) is inflated. Net (710) may comprise polyurethane, neoprene, and/or any other suitable material(s).

Net (710) has a mesh configuration that creates shallow dimples over the exterior of balloon (718). This allows mucus or other bodily fluid within an airway to be displaced around net (710) to increase the friction between balloon (718) and the airway to decrease or prevent slipping of balloon (718) within the airway. Net (710) may press against the mucosa lining hard enough to make some of the lining bulge through net (710) to provide a shear stress to increase traction. Net (710) may also increase the burst strength of balloon (718).

3. Exemplary Scoring Elements

FIGS. 15A-15B show another exemplary gripping assembly (800). Gripping assembly (800) comprises a balloon (818) and a scoring assembly (810) positioned around balloon (818). Balloon (818) is similar to balloon (18). Scoring assembly (810) comprises a proximal collar (812), a distal collar (816), and a plurality of scoring elements (826) extending between collars (812, 816). In the present example, scoring elements (826) are positioned in a helical configuration between collars (812, 816). However, other configurations may be used, such as a longitudinal configuration, as will be apparent to one with ordinary skill in the art in view of the teachings herein. Scoring elements (826) may have a sharp outward edge configured to engage the airway of a patient. Scoring elements (826) may be made from nitinol and/or any other suitable material(s).

Proximal collar (812) is configured to translate along proximal end (820) of balloon (818). Distal collar (816) is fixedly secured to distal end (821) of balloon (818). Scoring elements (826) are positioned over working length (824) of balloon (818) and are configured to expand as proximal collar (812) translates. For example, when proximal collar (812) is in a proximal position, as shown in FIG. 15A, scoring elements (826) are in a collapsed state. When proximal collar (812) is in a distal position, as shown in FIG. 15B, scoring elements (826) are in an expanded state. Proximal collar (812) may translate and scoring elements (826) may expand when balloon (818) is inflated, such that balloon (818) pushes scoring elements (826) to the expanded state. Alternatively, proximal collar (812) may translate and scoring elements (826) may expand separately from balloon (818). When scoring elements (826) are in the collapsed state, scoring elements (826) are sized to be smaller than an airway such that scoring elements (826) do not contact an airway during the delivery of balloon (818) to a target site. When scoring elements (826) expand, scoring elements (826) engage the airway of a patient to provide a grip and increase friction to decrease or prevent balloon (818) from slipping within the airway.

Figure 16A:
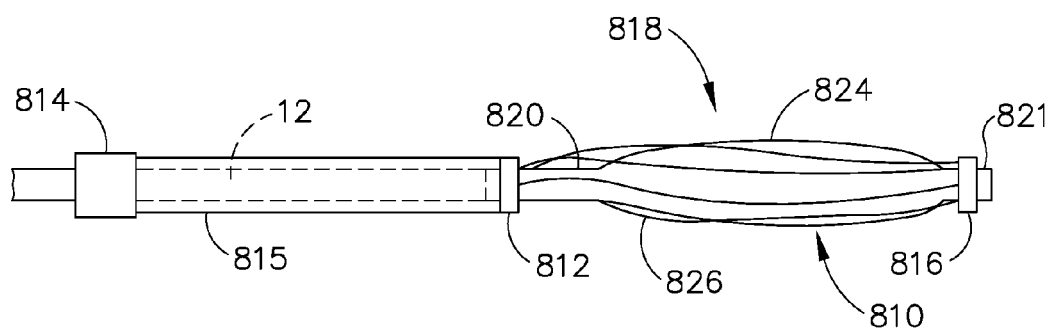
FIG. 16A depicts a side view of another exemplary balloon with a gripping assembly for use in the system of FIG. 1 in a collapsed configuration.
Figure 16B:
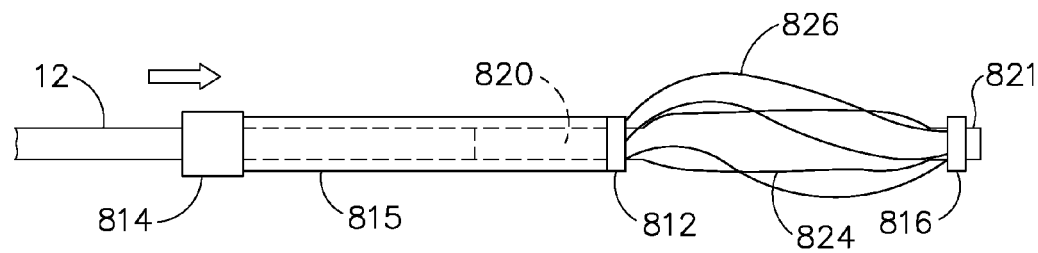
FIG. 16B depicts a side view of the balloon of FIG. 16A, showing the gripping assembly in an expanded configuration.
Figure 16C:
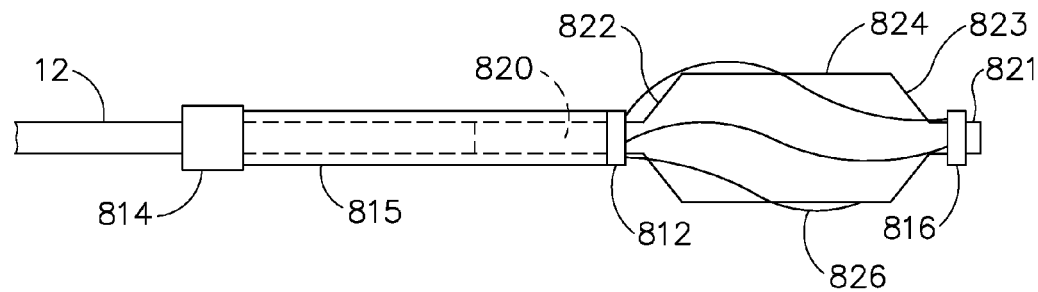
FIG. 16C depicts a side view of the balloon of FIG. 16A, showing the balloon in an expanded configuration.

In some versions, gripping assembly (800) may comprise a luer (814) or other feature, as shown in FIGS. 16A-16C, to actuate scoring elements (826). Luer (814) is positioned around shaft (12) of balloon catheter (10). Leur (814) is coupled to proximal collar (812) via shaft (815) positioned over shaft (12). Luer (814) is translatable relative to shaft (12). Shaft (815) is sufficiently rigid to communicate the translation of luer (814) to proximal collar (812). As shown in FIG. 16A, luer (814) is in a proximal position such that gripping assembly (800) is in a collapsed state. Balloon (818) is also deflated. Gripping assembly (800) is delivered through the airway to a targeted site in this collapsed configuration. As shown in FIG. 16B, luer (810) is translated to a distal position. This pushes proximal collar (812) distally via shaft (815) to push scoring elements (826) against distal collar (816) and expand scoring elements (826). Scoring elements (826) thus engage the airway in the expanded configuration to grip the airway. As shown in FIG. 16C, balloon (818) is then dilated within scoring elements (826) to treat the stenosis. Balloon (818) may also be dilated simultaneously with scoring elements (826), or balloon (818) may be dilated before scoring elements (826) such that balloon (818) pushes scoring elements (826) to expand. After balloon (818) is deflated, luer (814) is pulled proximally to collapse scoring elements (826) to facilitate the withdrawal of gripping assembly (800) from the airway.

C. Exemplary Dumbbell Shaped Balloon

Figure 17:
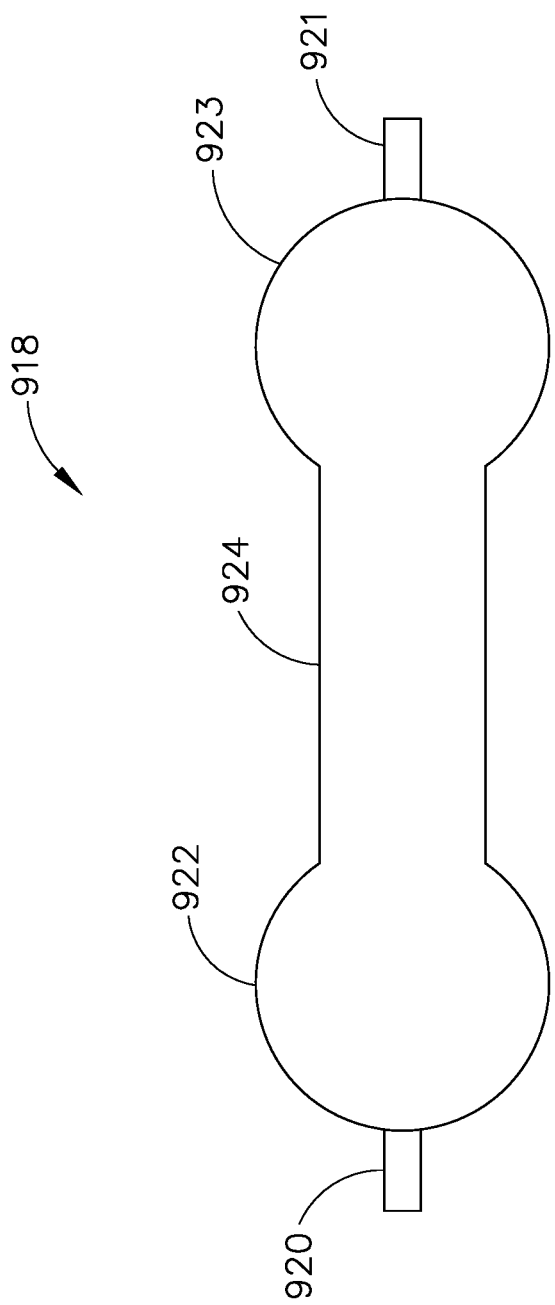
FIG. 17 depicts a side view of another exemplary balloon with gripping features for use in the system of FIG. 1.

The shape of a balloon (18) may also be modified to provide increased friction within an airway. For example, FIG. 17 shows an exemplary balloon (918) with a dumbbell configuration. Balloon (918) comprises a proximal end (920), an anchor portion (922), a working length (924), an anchor portion (923), and a distal end (921). Working length (924) is positioned between anchor portions (922, 923). In the present example, working length (924) and anchor portions (922, 923) form a single chamber. Anchor portions (922, 923) have a larger diameter than working length (924) when balloon (918) is dilated. For instance, anchor portions (922, 923) may expand to a diameter that is about 0.5 mm to about 2.5 mm larger than the diameter of working length (924), such as about 1.0 mm larger. Working length (924) is configured to treat a stenosis within an airway and may have a length of about 1.0 mm to about 15 mm. The wall thickness of working length (924) is about 0.001" to about 0.004" thick. Of course, any other suitable dimensions may be used.

Anchor portions (922, 923) are configured to engage the airway and increase the longitudinal stability of balloon (918) within the airway. Anchor portions (922, 923) would be positioned proximal and distal (respectively) to the stenosis (4), with working length (924) being positioned in the stenosis (4). Anchor portions (922, 923) have outer diameters that are greater than the inner diameter of the stenosis (4), such that anchor portions (922, 923) engage the ends of the stenosis (4) to hold working length (924) within the stenosis (4). The wall thickness of anchor portions (922, 923) may be less than the wall thickness of working length (924) such that anchor portions (922, 923) expand to a larger diameter when balloon (918) is dilated. Working length (924) may also be formed from a stiffer material than anchor portions (922, 923) such that anchor portions (922, 923) expand to a larger diameter when balloon (918) is dilated. Other suitable anchor portion (922, 923) configurations will be apparent to one with ordinary skill in the art in view of the teachings herein.

Figure 18:
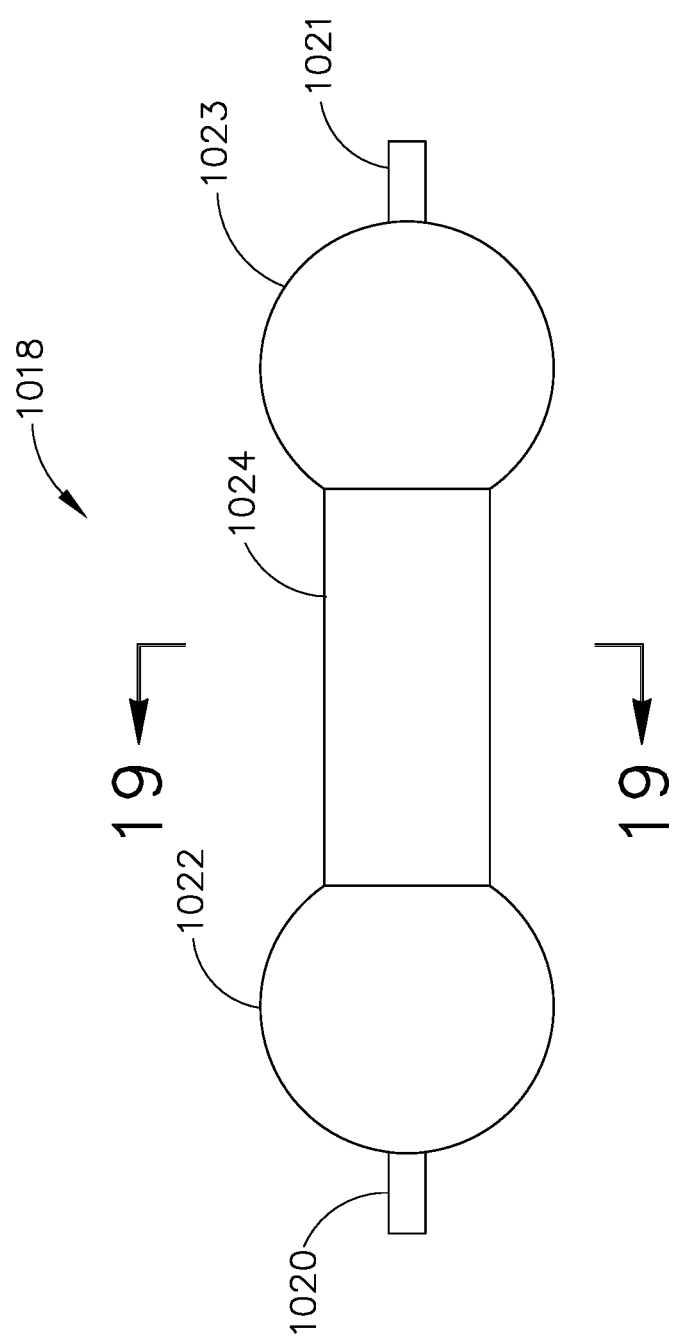
FIG. 18 depicts a side view of another exemplary balloon with gripping features for use in the system of FIG. 1.
Figure 19:
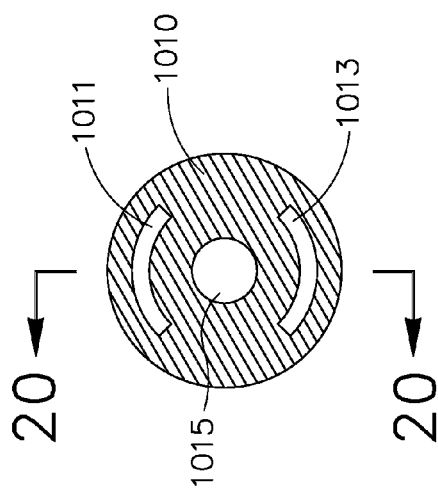
FIG. 19 depicts a cross sectional view of the balloon of FIG. 18 taken along line 19-19 of FIG. 18.
Figure 20:
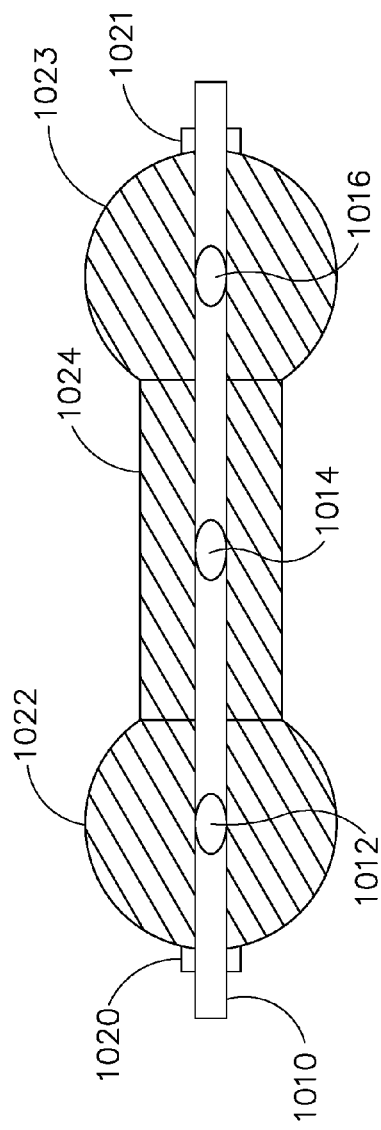
FIG. 20 depicts a cross sectional view of the balloon of FIG. 18 taken along line 20-20 of FIG. 19.

FIGS. 18-20 show another exemplary dumbbell shaped balloon (1018) having a plurality of chambers. Balloon (1018) is similar to balloon (918), except that anchor portion (1022), working length (1024), and anchor portion (1023) each has a separate chamber that may be inflated individually. Each chamber may be formed and then bonded together. Because each chamber may be inflated separately, each chamber may have its own compliance curve and diameter control. A shaft (1010), as shown in FIGS. 19 and 20, extends through balloon (1018). Shaft (1010) is coupled to shaft (12) of balloon catheter (10). As shown in FIG. 19, shaft (1010) comprises three lumens (1011, 1015, 1013), although any number of lumens may be used. In the present example, center lumen (1015) is used to insert an endoscope to provide visualization of the procedure, or as an air ventilation port. Top lumen (1011) is used to translate fluid to inflate anchor portions (1022, 1023). Bottom lumen (1013) is used to translate fluid to inflate working length (1024). As shown in FIG. 20, shaft (1010) comprises a port (1012) coupled with anchor portion (1022), a port (1014) coupled with working length (1024), and a port (1016) coupled with anchor portion (1023). Ports (1012, 1016) are open to lumen (1011) to fluidly couple anchor portions (1022, 1023) with lumen (1011). Port (1014) is open to lumen (1013) to fluidly couple working length (1024) with lumen (1013).

Accordingly, anchor portions (1022, 1023) and working length (1024) are inflated separately, which allows anchor portions (1022, 1023) and working length (1024) to be inflated at different times and to different diameters. For instance, balloon (1018) may be inserted within a stenosis (4) in a deflated state. Fluid may then be translated through lumen (1011) to inflate anchor portions (1022, 1023) to a sufficient diameter to engage the airway on either side of the stenosis (4). Once anchor portions (1022, 1023) are inflated to hold balloon (1018) longitudinally in place within the airway, fluid may then be translated through lumen (1013) to inflate working length (1024). Working length (1024) may be inflated to a smaller diameter than anchor portions (1022, 1023) to expand the stenosis (4). Although anchor portions (1022, 1023) are connected to lumen (1011) in the present example, anchor portions (1022, 1023) may also have separate lumens to inflate anchor portions (1022, 1023) individually. Other suitable lumen configurations will be apparent to one with ordinary skill in the art in view of the teachings herein.

D. Exemplary Balloon Positioning System

Figure 21:
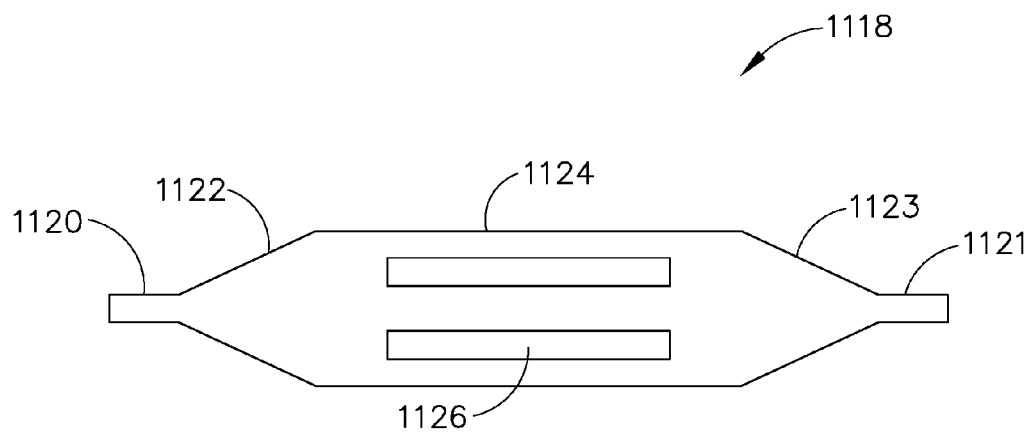
FIG. 21 depicts a side view of another exemplary balloon with gripping features for use in the system of FIG. 1.
Figure 22:
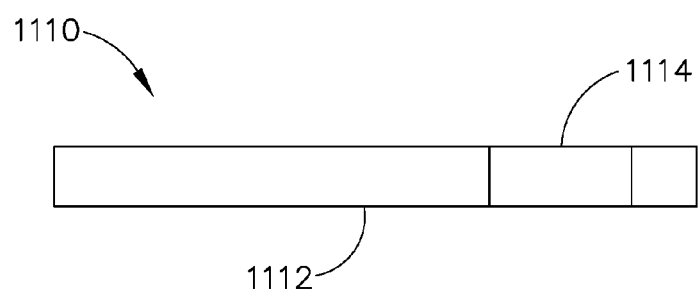
FIG. 22 depicts a side view of an exemplary positioning device for use with the balloon of FIG. 21.

FIGS. 21-23B show an exemplary balloon positioning system (1100). Balloon positioning system (1100) comprises a balloon (1118) and a positioning device (1110). As shown in FIG. 21, balloon (1118) is similar to balloon (18), except that balloon (1118) comprises a plurality of magnetic elements (1126). Elements (1126) are magnetic and are applied to the surface of working length (1124). Any number, shape, and configuration of elements (1126) may be used. As shown in FIG. 22, positioning device (1110) comprises a magnetic portion (1114) positioned on a distal end of shaft (1112). Magnetic portion (1114) is configured to attract to magnetic elements (1126) of balloon (1118) with a force sufficient to decrease or prevent movement of balloon (1118) within an airway. Magnetic portion (1114) and magnetic elements (1126) may be permanent magnets (e.g., a rare earth metal, etc.), or electromagnets. If electromagnets are used, the magnetic portion (1114) and/or elements (1126) may be selectively activated and the force of magnetic portion (1114) and/or magnetic elements (1126) may be adjusted. It should also be understood that some versions may use just one magnet. For instance, balloon (1118) may just include a ferromagnetic material while positioning device (1110) includes a magnet (e.g., a permanent magnet such as a neodymium iron boron (NdFeB or NIB), samarium cobalt (SmCo), alnico, ceramic, or ferrite; or an electromagnet, etc.).

Figure 23A:
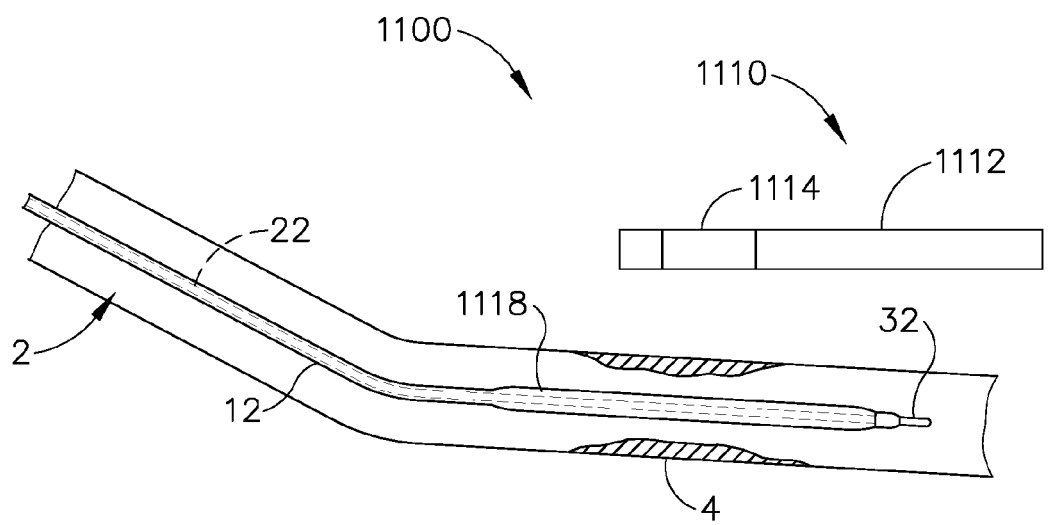
FIG. 23A depicts a cross sectional view of an exemplary system with the balloon of FIG. 21 being introduced into an airway, with the balloon positioned at a stenosis in a collapsed state with the positioning device positioned over the balloon.
Figure 23B:
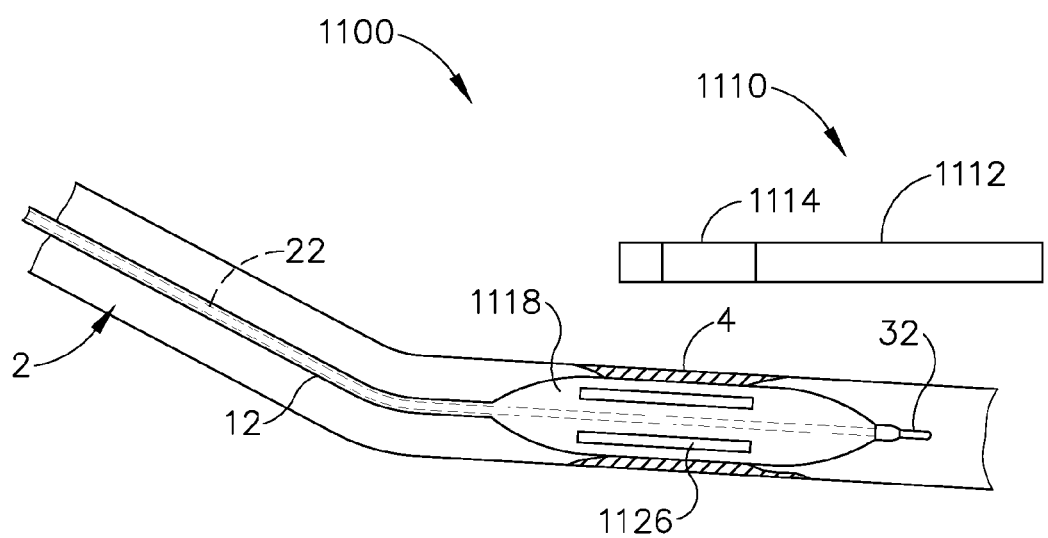
FIG. 23B depicts a cross sectional view of the system of FIG. 23A, with the balloon inflated to a dilated state.

In an exemplary use, as shown in FIGS. 23A-23B, balloon positioning system (1100) is used to position balloon (1118) at a target site within an airway. As shown in FIG. 23A, balloon (1118) is in a deflated state and is introduced through an airway (2) to a target site within a stenosis (4). Positioning device (1110) is positioned outside airway (2) such that magnetic portion (1114) is above the target site. Positioning device (1110) may be positioned within the body, or external to the body. Magnetic portion (1114) attracts magnetic elements (1126) such that magnetic elements (1126) are introduced through airway (2) with balloon (1118) until magnetic elements (1126) are adjacent to magnetic portion (1114). This provides the desired location of balloon (1118). Alternatively, balloon (1118) may be moved to position within stenosis (4), then positioning device (1110) may be moved to position magnetic portion (1114) near magnetic elements (1126). Balloon (1118) may then be inflated. As shown in FIG. 23B, balloon (1118) is then dilated to expand the blocked region of airway (2). The force between magnetic portion (1114) and magnetic elements (1126) retain balloon (1118) at its longitudinal position within airway (2) to decrease or prevent balloon (1118) from slipping when balloon (1118) is dilated. Positioning device (1110) may be moved away before or after deflation of balloon (1118) to enable removal of balloon (1118) from airway (2).

As one merely illustrative variation of system (1100), magnetic portion (1114) may be incorporated into a variation of stylet (22) instead of an external positioning device (1110). The modified stylet (22) may remain disposed within catheter (10) and may be held stationary during inflation of balloon (1118). A magnetic portion of the modified stylet (22) may be attracted to a ferrous or magnetic portion of balloon (1118) or catheter (10) to prevent longitudinal movement of balloon (1118) during inflation. Still other suitable variations will be apparent to those of ordinary skill in the art in view of the teachings herein.

III. Miscellaneous

As noted above, the exemplary variations of balloons and other components described herein may be readily incorporated into a sinuplasty system, such that the balloons described herein may be used to dilate an ostium of a sinus. By way of example only, the exemplary variations of balloons and other components described herein may be readily combined with various teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. As yet another merely illustrative example, the exemplary variations of balloons and other components described herein may be readily incorporated into a Relieva® Spin Balloon Sinuplasty™ System by Acclarent, Inc. of Menlo Park, Calif.

Other suitable ways in which the teachings herein may be applied to the sinus dilation context and/or other anatomical passageway dilation contexts will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation assembly, wherein the dilation assembly comprises:
    (a) a shaft defining a longitudinal axis, wherein the shaft comprises a distal end and a proximal end; and
    (b) a dilator coupled with the distal end of the shaft, wherein the dilator comprises:
        (i) a proximal end,
        (ii) a distal end,
        (iii) a center portion positioned between the proximal end and the distal end, wherein the center portion is dilatable to have a larger diameter than the proximal end and the distal end, wherein the center portion is configured to dilate from a first configuration to a second configuration,
        (iv) a plurality of working length portions defined by the center portion, and
        (v) a plurality of elongate gripping features positioned on the center portion, wherein each of the elongate gripping features is folded under each respective working length portion when the dilator is in the first configuration, wherein a majority of each of the gripping features is configured to be in atraumatic direct contact with a bodily lumen to provide friction between the center portion of the dilator and the bodily lumen when the center portion is in the second configuration, wherein the gripping features are symmetrical about the longitudinal axis in the first configuration.

2. The dilation assembly of claim 1, wherein the gripping features are symmetrical about the longitudinal axis in the second configuration.

3. The dilation assembly of claim 1, wherein the gripping features are configured to pivot relative to the center portion in response to the center portion dilating from the first configuration to the second configuration.

4. The dilation assembly of claim 3, wherein each the gripping features is configured to pivot in the same direction as the other of the gripping features in response to the center portion dilating from the first configuration to the second configuration.

5. The dilation assembly of claim 1, wherein the gripping features are wrapped around the center portion in the first configuration.

6. The dilation assembly of claim 1, wherein the working length portions include a lower coefficient of friction than the gripping features.

7. The dilation assembly of claim 1, wherein the working length portions include a lubricious coating.

8. The dilation assembly of claim 1, wherein the gripping features are configured to be exposed to increase friction between the balloon and an airway.

9. The dilation assembly of claim 1, wherein the gripping features are spaced apart from each other along alternating working length portions.

10. The dilation assembly of claim 1, wherein the gripping features are disposed parallel to one another.

11. The dilation assembly of claim 1, wherein the gripping features are resiliently biased toward the longitudinal axis when the dilator is in the first configuration.

12. The dilation assembly of claim 1, wherein the gripping features comprise an elastomeric material.

13. The dilation assembly of claim 1, wherein the gripping features comprise a fabric.

14. The dilation assembly of claim 1, wherein the gripping features are positioned about the axis such that the gripping features comprise a plurality of folds.

15. A dilation assembly, wherein the dilation assembly comprises:
   (a) a shaft defining a longitudinal axis, wherein the shaft comprises a distal end and a proximal end; and
   (b) a dilator coupled with the distal end of the shaft, wherein the dilator comprises:
      (i) a proximal end,
      (ii) a distal end,
      (iii) a center portion positioned between the proximal end and the distal end, wherein the center portion is dilatable to have a larger diameter than the proximal end and the distal end, wherein the center portion is configured to dilate from a first configuration to a second configuration,
      (iv) a plurality of working length portions defined by the center portion, wherein the working length portions include a lower coefficient of friction than the gripping features, and
      (v) a plurality of elongate gripping features positioned on the center portion, wherein each of the elongate gripping features is folded under each respective working length portion when the dilator is in the first configuration, wherein a majority of each of the gripping features is configured to be in atraumatic direct contact with a bodily lumen to provide friction between the center portion of the dilator and the bodily lumen when the center portion is in the second configuration, wherein the gripping features are configured to pivot to an exposed position in response to the center portion dilating from the first configuration to the second configuration.

16. The dilation assembly of claim 15, wherein each of the gripping features is positioned between a pair of working length portions, wherein the working length portions comprise a lubricious coating.

17. The dilation assembly of claim 15, wherein each of the gripping features is angularly spaced a first amount from an adjacent one of the gripping features in the first configuration, wherein each of the gripping features is angularly spaced the first amount from an adjacent one of the gripping features in the second configuration.

18. A dilation assembly, wherein the dilation assembly comprises:
   (a) a shaft defining a longitudinal axis, wherein the shaft comprises a distal end and a proximal end; and
   (b) a dilator coupled with the distal end of the shaft, wherein the dilator comprises:
      (i) a proximal end,
      (ii) a distal end,
      (iii) a center portion positioned between the proximal end and the distal end, wherein the center portion is dilatable to have a larger diameter than the proximal end and the distal end, wherein the center portion is configured to dilate from a first configuration to a second configuration,
      (iv) a plurality of working length portions defined by the center portion, wherein the working length portions include a lubricious coating, and
      (v) a plurality of elongate gripping features positioned on the center portion, wherein each of the gripping features is folded under each respective working length portion when the dilator is in the first configuration, wherein a majority of each of the gripping features is configured to be in atraumatic direct contact with a bodily lumen to provide friction between the center portion of the dilator and the bodily lumen when the center portion is in the second configuration.

19. The dilation assembly of claim 17, wherein the gripping features are spaced from the center portion in the second configuration.

20. The dilation assembly of claim 15, wherein each of the working length portions is exposed, and not hidden by, the gripping features in both the first and second configurations.

\* \* \* \* \*